(12) United States Patent
Tanabe

(10) Patent No.: US 10,168,224 B2
(45) Date of Patent: Jan. 1, 2019

(54) APPARATUS AND METHOD FOR CONTROLLING FREQUENCY ANALYSIS PROCESSING, AND SENSOR MODULE

(71) Applicant: FUJITSU LIMITED, Kawasaki-shi, Kanagawa (JP)

(72) Inventor: Satoshi Tanabe, Meguro (JP)

(73) Assignee: FUJITSU LIMITED CO., LTD., Kawasaki (JP)

( * ) Notice: Subject to any disclaimer, the term of this patent is extended or adjusted under 35 U.S.C. 154(b) by 13 days.

(21) Appl. No.: 15/417,448

(22) Filed: Jan. 27, 2017

(65) Prior Publication Data

US 2017/0268932 A1  Sep. 21, 2017

(30) Foreign Application Priority Data

Mar. 15, 2016 (JP) ................... 2016-051625

(51) Int. Cl.
| | | |
|---|---|---|
| *G06F 19/00* | (2018.01) | |
| *G01J 11/00* | (2006.01) | |
| *G01J 1/02* | (2006.01) | |
| *A61B 5/024* | (2006.01) | |
| *A61B 5/00* | (2006.01) | |

(52) U.S. Cl.
CPC ............. *G01J 11/00* (2013.01); *A61B 5/024* (2013.01); *A61B 5/7257* (2013.01); *G01J 1/0228* (2013.01); *A61B 5/0002* (2013.01); *A61B 5/02416* (2013.01)

(58) Field of Classification Search
CPC . A61B 5/7257; A61B 5/7275; A61B 5/02042; A61B 5/021
USPC ................... 702/179, 180, 182–185
See application file for complete search history.

(56) References Cited

U.S. PATENT DOCUMENTS 6,662,130 B1 * 12/2003 Peel, III ................ A61B 5/021
                                                600/485
7,088,765 B1 *  8/2006 Green ................... H04L 27/364
                                                375/142

FOREIGN PATENT DOCUMENTS

JP       2002-222177        8/2002

* cited by examiner

*Primary Examiner* — Edward Raymond
(74) *Attorney, Agent, or Firm* — Staas & Halsey LLP

(57) ABSTRACT

An apparatus for controlling a frequency analysis processing includes: a memory; and a processor coupled to the memory and configured to execute a fast Fourier transform process that includes performing a fast Fourier transform operation on data of two groups into which sensor data sensed at a first sampling frequency by a sensor is divided, and execute a change process that includes changing, in a case where results of butterfly operations of the fast Fourier transform operation are similar between the two groups, a sampling frequency at which the sensor operates to a second sampling frequency lower than the first sampling frequency.

15 Claims, 16 Drawing Sheets

APPARATUS AND METHOD FOR CONTROLLING FREQUENCY ANALYSIS PROCESSING, AND SENSOR MODULE

CROSS-REFERENCE TO RELATED APPLICATION

This application is based upon and claims the benefit of priority of the prior Japanese Patent Application No. 2016-051625, filed on Mar. 15, 2016, the entire contents of which are incorporated herein by reference.

FIELD

The embodiments discussed herein are related to an apparatus and a method for controlling a frequency analysis processing, and a sensor module.

BACKGROUND

Frequency analysis of sensor data is usefully used in a wide variety of situations. For example, in the case of an optical pulse wave sensor, data acquired from the pulse wave sensor, for example, a signal associated with a strength of light transmitted through or reflected from a measurement target part is subjected to a frequency analysis such as a fast Fourier transform, and a peak value of a frequency spectrum obtained as a result of the frequency analysis is determined thereby detecting a pulse rate.

In a case where data acquired from the pulse wave sensor is all transmitted to a particular output destination such as a desktop computer, a server apparatus, or the like, this causes an increase in power consumed in wireless communication. To handle the above situation, a function of frequency analysis may be provided in the sensor and a pulse rate may be transmitted instead of transmitting all sensor data thereby reducing the power consumed in the wireless communication.

In a case where a sensor module is realized by implementing the function of frequency analysis in the sensor, the sensor module may be used in a wearable device such as a band-type device, or may be used to provide one of functions of a smartphone or the like. As an example of the related art, a technique disclosed in Japanese Laid-open Patent Publication No. 2002-222177 is known.

SUMMARY

According to an aspect of the invention, an apparatus for controlling a frequency analysis processing includes: a memory; and a processor coupled to the memory and configured to execute a fast Fourier transform process that includes performing a fast Fourier transform operation on data of two groups into which sensor data sensed at a first sampling frequency by a sensor is divided, and execute a change process that includes changing, in a case where results of butterfly operations of the fast Fourier transform operation are similar between the two groups, a sampling frequency at which the sensor operates to a second sampling frequency lower than the first sampling frequency.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

In conventional techniques, there may still be a situation in which it is difficult to reduce consumption power of a sensor module.

For example, in the case of an optical pulse wave sensor, emitting light from an LED may cause an increase in consumption power, which may be a demerit. For example, typical consumption power of a conventional pulse wave sensor is about 5 mW. In this case, to operate the pulse wave sensor for a period of 60 seconds, as large energy as 300 mJ is consumed by the pulse wave sensor. Furthermore, the frequency analysis performed by the sensor module, that is the fast Fourier transform operation also consumes large power, which results in an increase in the total consumption power of the sensor module. Such an increase in consumption power of the sensor module may be more serious as it becomes more popular to use the sensor module in an environment in which available power is limited as with a wearable device, a smartphone, or the like.

As one aspect of the present embodiment, provided are solutions for being able to reduce consumption power of the sensor module.

A frequency analysis apparatus, a frequency analysis method, and a sensor module according to the present disclosure are described below with reference to accompanying drawings. Note that the technique according to the present disclosure is not limited to those embodiments described below. Also note that two or more embodiments may be combined as long as no inconsistency occurs in a resultant process.

First Embodiment

Figure 1:
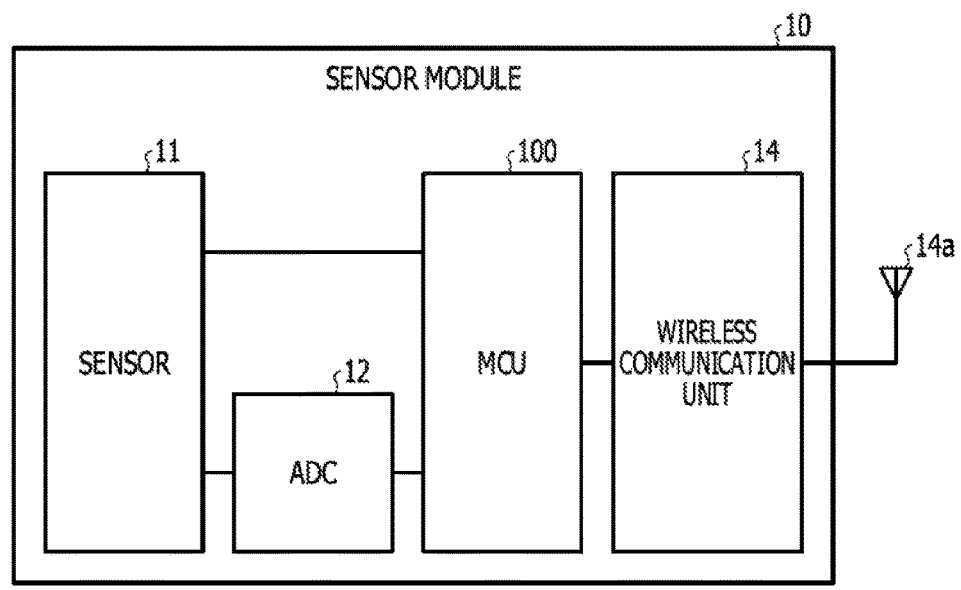
FIG. 1 is a block diagram illustrating a functional configuration of a sensor module according to a first embodiment.

FIG. 1 is a block diagram illustrating a functional configuration of a sensor module according to a first embodiment. The sensor module 10 illustrated in FIG. 1 may be implemented, for example, as a built-in system for performing frequency analysis of sensor data.

The sensor module 10 illustrated in FIG. 1 performs a frequency analysis process including a fast Fourier transform on data of two groups into which sensor data obtained at a first sampling frequency is divided. In the frequency analysis process, if results of butterfly operations thereof are similar between the two groups, the sampling frequency at which the sensor and the like operate is changed to a second sampling frequency lower than the first sampling frequency. This makes it possible, in an aspect, to reduce the frequency of occurrences of an Analog-to-Digital Converter (ADC) operation to convert data in the sensor and data input from a sensor from analog form to digital form, thereby achieving a reduction in consumption power of the sensor module 10.

As illustrated in FIG. 1, the sensor module 10 includes a sensor 11, an analog-to-digital converter (ADC) 12, a microcomputer (MCU) 100, and a wireless communication unit 14. Although in FIG. 1, a built-in system is illustrated as an example, the embodiment may be implemented in a general-purpose computer system.

The sensor 11 is a device configured to perform various kinds of sensing operations.

In the following description, it is assumed by way of example that an optical pulse wave sensor is included as a sensor in the sensor module 10. However, the sensor is not limited to the optical pulse wave sensor, but any type of sensor configured to generate sensor data used in frequency analysis may be employed.

In a case where the optical pulse wave sensor is used as the sensor 11, the optical pulse wave sensor may be of a transmission type or a reflection type. In the case of the transmission-type pulse wave sensor, a measurement object may be placed between a light emitting part and a light receiving part. In the case of the reflection-type pulse wave sensor, the pulse wave sensor may be attached to a measurement object. In the sensor 11, light with a particular wavelength such as that in a wavelength range in which light is absorbed by hemoglobin is emitted from the light emitting part such as a light emitting diode (LED), and transmitted light or reflected light is sensed by the light receiving part. In this way, continuous data associated with light intensity is obtained as an analog signal.

The ADC 12 is a device such as an electronic circuit configured to convert the analog signal to a digital signal.

For example, the ADC 12 performs sampling, at a fixed time intervals, on the strength of the analog signal input from the sensor 11, and quantizes the resultant values to convert them into digital signals. As a result, the continuous data associated with the light intensity is converted into discrete data. Note that the frequency at which the sampling is performed by the ADC 12 is not necessarily fixed. That is, the ADC 12 operates according to, at least, the first sampling frequency and the second sampling frequency as described above. That is, the sampling frequency at which the ADC 12 operates is changed under the control of the MCU 100.

The MCU 100 is a device configured to control the whole sensor module 10.

For example, the MCU 100 may be implemented using integrated circuits including a central processing unit (CPU), a random access memory (RAM) serving as a main storage apparatus, and other peripheral devices. The MCU 100 has a function of controlling hardware disposed in the sensor module 10. Furthermore, the MCU 100 is configured to include a processing unit that is virtually realized by executing a program so as to be capable of performing the frequency analysis process as will be described in further detail later.

The wireless communication unit 14 is a processing unit configured to perform wireless communication via an antenna 14a.

For example, the wireless communication unit 14 may be configured to perform communication via a medium such as a radio wave, light, an ultrasonic wave, or the like. A communication method employed by the wireless communication unit 14 may be, for example, a wireless local area network (LAN) communication method, a long term evolution (LTE) communication method, or any other carrier communication method.

For example, under the control of the MCU 100, the wireless communication unit 14 transmits data output from the MCU 100 to a particular output destination. In a case where the pulse wave sensor is used as the sensor 11, an example of data transmitted by the wireless communication unit 14 is data indicating a peak value of a frequency spectrum obtained by converting the input data into a frequency domain, that is, a pulse rate, or the like. An example of the data output destination is a general information processing apparatus such as a desktop computer, a server apparatus, or the like. In a case where the information processing apparatus includes a diagnostic program installed thereon for diagnosing functionality of autonomic nerves, cardiac disease, or the like from a fluctuation of the pulse rate or the pulse period, it is possible to obtain a result of diagnosis of a user performed by the diagnostic program.

<Configuration of MCU 100> The MCU 100 illustrated in FIG. 1 virtually realizes processing units described below by loading a frequency analysis program, installed as a program for realizing the frequency analysis process, in a work area of a RAM (not illustrated) as a process.

Figure 2:
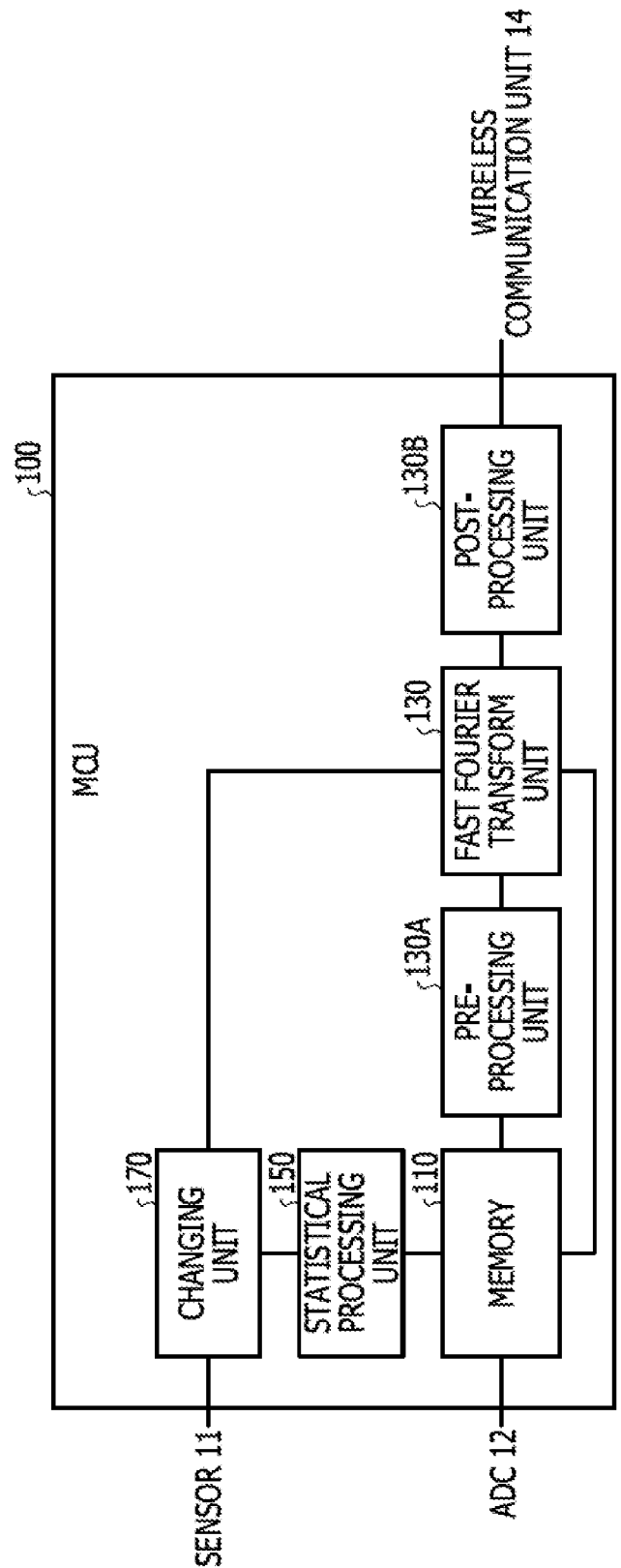
FIG. 2 is a block diagram illustrating a functional configuration of an MCU according to the first embodiment.

FIG. 2 is a block diagram illustrating a functional configuration of the MCU 100 according to the first embodiment. As illustrated in FIG. 2, the MCU 100 includes a memory 110, a pre-processing unit 130A, a fast Fourier transform unit 130, a post-processing unit 130B, a statistical processing unit 150, and a changing unit 170.

The memory 110 is a storage apparatus configured to store various kinds of data.

For example, the memory 110 may be, for example, a semiconductor memory device such as a RAM, a DRAM, or the like. For example, sensor data output from the ADC 12 is given as input data to the memory 110 and stored therein. A butterfly operation result output from the fast Fourier transform unit 130 is also stored in the memory 110.

The pre-processing unit 130A and the post-processing unit 130B are processing units configured to perform pre-processing or post-processing of the frequency analysis.

For example, in a case where the optical pulse wave sensor is employed as the sensor 11, the pre-processing unit 130A performs a filtering process such as an average filtering process on the input data read out from the memory 110. The post-processing unit 130B performs a process to determine a peak value from the frequency spectrum obtained as a result of the fast Fourier transform performed by the fast Fourier transform unit 130. Although it is assumed by way of example that the input data is given by an output from the pulse wave sensor, other processes may be performed as the pre-processing or post-processing depending on the type of the sensor or the type of input data. Note that both the pre-processing unit 130A and the post-processing unit 130B may not be provided, but only one of them may be provided or none of the pre-processing unit and post-processing unit may be provided.

The fast Fourier transform unit 130 is a processing unit configured to perform a fast Fourier transform (FFT).

In the present example, the FFT refers to an algorithm of performing a high-speed calculation of a discrete Fourier transform (DFT) on a computer. The discrete Fourier transform may be defined by formula (1) described below. In formula (1), x(n) denotes input data, and X(k) denotes output data, that is, a result of the Fourier transform operation. N denotes the number of pieces of input data, and n and k respectively denote indexes of input data and output data. Furthermore, j denotes an imaginary unit and pi denotes π. In formula (1) described below, if an exponential function $\exp((-j2pi/N) \cdot n \cdot k)$ is replaced by $W_N^{n \cdot k}$, then formula (1) is rewritten as formula (2).

$$X[k] = \sum_{n=0}^{N-1} \{x[n] \cdot \exp((-j2pi/N) \cdot n \cdot k)\} \quad (1)$$

$$= \sum_{n=0}^{N-1} \{x[n] \cdot W_N^{n \cdot k}\} \quad (2)$$

In formula (2) described above, the N-point time-series input data is divided into two groups such that one group includes even-numbered data and the other includes odd-numbered data as described in formula (3). Furthermore, because the twiddle factor W has periodicity as described below in formula (4), that is, because the twiddle factor W is symmetric in the complex plane, formula (2) described above can be rewritten as formula (5). In formula (5), if a result of a butterfly operation for even-numbered N/2 points is denoted as G[k], and a result of a butterfly operation for odd-numbered N/2 points is denoted as H[k], then formula (5) is rewritten as formula (6). That is, N-point DFT is divided into two N/2-point DFTs.

Figure 3:
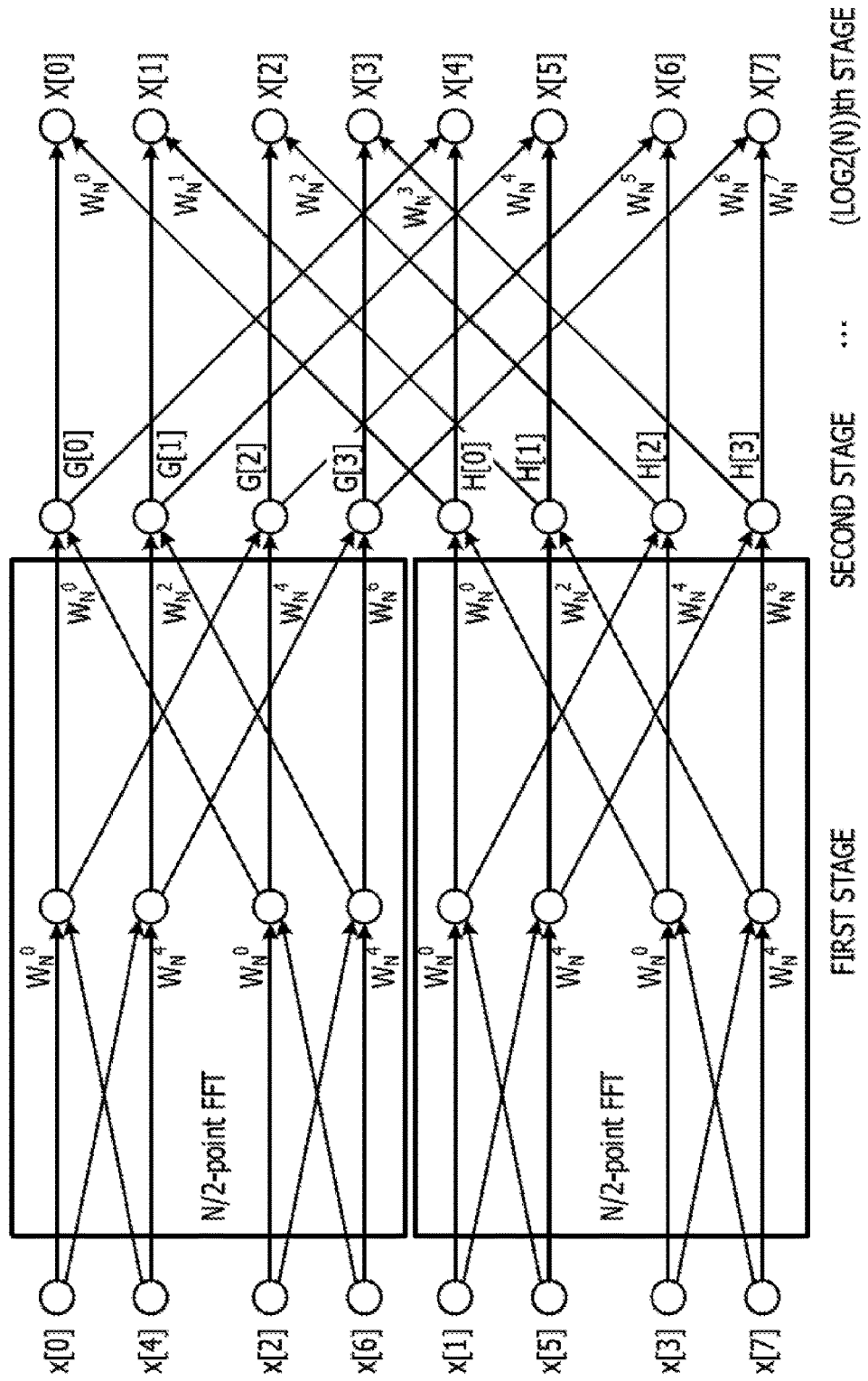
FIG. 3 is a diagram illustrating an example of a signal flow.

FIG. 3 is a diagram illustrating an example of a signal flow. In FIG. 3, the signal flow is illustrated by way of example for a case where N=8. In FIG. 3, x(0) to x(7) indicate input data, and X(0) to X(7) indicate results of FFT operations. Furthermore, in FIG. 3, WN0 to WN7 indicate twiddle factors in the FFT operation. As illustrated in the signal flow in FIG. 3, a calculation is performed to determine the sum of the results G[k] of FFT butterfly operations for even-numbered N/2 points at a $(\log_2(N)-1)$th stage (the second stage in this specific case) and results H[k] of FFT butterfly operations for odd-numbered N/2 points at the $(\log_2(N)-1)$th stage (the second stage in this specific case) multiplied by twiddle factors Wk, thereby obtaining output data X(0) to X(7).

$$\begin{cases} W_N^m = \exp((-j2pi/N) \cdot m) \\ W_N^N = 1, W_N^{N/2} = -1 \end{cases} \quad (3)(4)$$

$$X[k] = \sum_{m=0}^{N/2-1} \{x[2m] \cdot W_{N/2}^{k \cdot m}\} + W_N^k \cdot \sum_{m=0}^{N/2-1} \{x[2m+1] \cdot W_{N/2}^{k \cdot m}\} \quad (5)$$

-continued
$$= \underbrace{G[k] + W_N^k \cdot H[k]}_{\text{Butterfly Operation}} \quad (6)$$

G[k] and H[k] are respectively discrete Fourier transforms of even-numbered data and odd-numbered data, and thus it is possible to divide them in a similar manner as described in formula (7) and formula (8). By repeating the above process, it is possible to finally expand them in the form of 2-point DFT. As a result, a signal flow from the first stage to the $(\log_2(N))$th stage is obtained.

$$G[k] = \sum_{l=0}^{N/4-1} \{x[4l] \cdot W_{N/4}^{k \cdot l}\} + W_{N/2}^k \cdot \sum_{l=0}^{N/4-1} \{x[4l+2] \cdot W_{N/4}^{k \cdot l}\} \quad (7)$$

$$H[k] = \sum_{l=0}^{N/4-1} \{x[4l+1] \cdot W_{N/4}^{k \cdot l}\} + W_{N/2}^k \cdot \sum_{l=0}^{N/4-1} \{x[4l+3] \cdot W_{N/4}^{k \cdot l}\} \quad (8)$$

As described above, the fast Fourier transform unit 130 is capable of obtaining results of FFT operations for N points by performing butterfly operations according to the signal flow from the first stage to the $(\log_2(N))$th stage. Each time the fast Fourier transform unit 130 obtains a result of N-point FFT operation, the fast Fourier transform unit 130 stores results of butterfly operations of even-numbered N/2 points, that is, G[k], and results of butterfly operations of odd-numbered N/2 points, that is, H[k], in the memory 110.

The amount of FFT operation O(N) is given by the sum of the number of product operations and the number of addition operations, as described in formula (9). In formula (9), M(N) denotes the number of product operations, and A(N) denotes the number of addition operations. M(N) is given by $N \cdot \log_2(N)$ as described in formula (10) and formula (11), and A(N) is also given by $N \cdot \log_2(N)$ as described in formula (12) and formula (13). Therefore, the amount of FFT operation O(N) is given by $2N \cdot \log_2(N)$ as described in formula (14).

$$O(N) = M(N) + A(N) \quad (9)$$
$$= 2N \cdot \log_2 N \quad (14)$$
$$\begin{cases} M(N) = 2 \cdot M(N/2) + N & (10) \\ \quad = N \cdot \log_2(N) & (11) \\ A(N) = 2 \cdot A(N/2) + N & (12) \\ \quad = N \cdot \log_2(N) & (13) \end{cases}$$

Referring again to FIG. 2, the statistical processing unit 150 is a processing unit configured to perform various kinds of statistical processes.

In an aspect, the statistical processing unit 150 performs a regression analysis on results of butterfly operations performed in the past by the fast Fourier transform unit 130. For example, the statistical processing unit 150 reads out results of butterfly operations at the $(\log_2(N)-1)$th stage stored in the memory 110 over a particular number of generations, for example, M generations. Thereafter, the statistical processing unit 150 estimates a linear regression model described in formula (15) according to a multiple least-square regression formula described in formula (16). In the example described in formula (16), the least square method is applied to data (T=T1, ... TM) over M generations in the past.

$$\begin{pmatrix} H[0] \\ H[1] \\ \vdots \\ H[N/2-1] \end{pmatrix}_H = \begin{pmatrix} b_1 & & 0 \\ & b_2 & \\ & & \ddots \\ 0 & & b_{N/2} \end{pmatrix}_B \begin{pmatrix} G[0] \\ G[1] \\ \vdots \\ G[N/2-1] \end{pmatrix}_G + \begin{pmatrix} a_1 \\ a_2 \\ \vdots \\ a_{N/2} \end{pmatrix}_A \quad (15)$$

$$\Delta_H^2[j] = \sum_{k=1}^{M} \{H[j](T=T_k) - b_j \cdot G[j](T=T_k) - a_j\}^2 \quad (16)$$

As described above, in the case where the regression formula described in formula (16) is used, the statistical processing unit 150 solves formula (17) and formula (18) described below to estimate the intercept aj and the inclination bj in the linear regression model. In this case, H[j] in formula (16) is given by formula (19) described below. Furthermore, E(H[j]) in formula (19) described below is given by formula (20), Sxy[j] in formula (19) is given by formula (21), and Sx[j] in formula (19) is given by formula (22) described below.

$$\text{Solve the following equations to determine } a_j \text{ and } b_j \begin{cases} \dfrac{\partial \Delta_H^2[j]}{\partial a_j} = 0 & (17) \\ \dfrac{\partial \Delta_H^2[j]}{\partial b_j} = 0 & (18) \end{cases}$$

$$H[j] = E(H[j]) + (S_{xy}[j]/S_x[j]^2) \cdot (G[j] - E(G[j])) \quad (19)$$

$$\begin{cases} E(H[j]) = 1/M \cdot \sum_{k=1}^{M} \{H[j](T=T_k)\} & (20) \\ S_{xy}[j] = 1/M \cdot \sum_{k=1}^{M} \{H[j](T=T_k) \cdot G[j](T=T_k)\} - E(H[j]) \cdot E(G[j]) & (21) \\ S_x[j] = 1/M \cdot \sum_{k=1}^{M} \{G[j](T=T_k) - E(G[j])\} & (22) \end{cases}$$

As described above, the statistical processing unit 150 is capable of estimating the intercept aj and the inclination bj by solving a problem given by formula (17) and formula (18).

In the present example, under the assumption that H[j] is an independent variable and G[j] is a dependent variable, the intercept aj and the inclination bj of the linear regression model are estimated. However, the linear regression model may be estimated under the assumption that the H[j] is a dependent variable and G[j] is an independent variable. Furthermore, although in the present example, the linear regression model is estimated, a nonlinear regression model may be estimated.

In another aspect, in addition to estimating the regression model, the statistical processing unit 150 calculates similarity of data between two groups, that is, similarity between results of butterfly operations for even-numbered data and those for odd-numbered data. More specifically, for example, to determine the similarity, the statistical processing unit 150 calculates a correlation coefficient S[j] between G[j] (T=Tk) and H[j] (T=Tk) according to formula (23) described below.

$$S[j] = \dfrac{\sum_{k=1}^{M} (G[j](T=T_k) - E(G[j])) \cdot (H[j](T=T_k) - E(H[j]))}{\left( \sum_{k=1}^{M} (G[j](T=T_k) - E(G[j]))^2 \cdot \sum_{k=1}^{M} (H[j](T=T_k) - E(H[j]))^2 \right)^{1/2}} \quad (23)$$

A result {aj, bj, Sj} obtained as a result of the statistical process performed in the above described manner by the statistical processing unit 150 is output to the changing unit 170.

The changing unit 170 is a processing unit configured to change at least one of the sampling frequency at which the sensor 11 operates and the algorithm used in the fast Fourier transform by the fast Fourier transform unit 130.

For example, the changing unit 170 determines whether the degree of similarity between results of the butterfly operations for the even-numbered data and those for the odd-numbered data is equal to or grater than a predetermined threshold value. More specifically, for example, the changing unit 170 determines whether the correlation coefficient Sj is equal to or greater than 0.7.

In a case where the correlation coefficient Sj is equal to or greater than 0.7, it is determined that there is a high probability that the accuracy of the result of the calculation of H[k] using the linear regression model is equal to or higher than a particular level. In this case, the changing unit 170 changes the sampling frequency at which the sensor 11 and the ADC 12 operate to the second sampling frequency. More specifically, for example, in a case where the first sampling frequency is the sampling frequency at which the input data used in the signal flow illustrated in FIG. 3 is sensed, the changing unit 170 changes the sampling frequency to one-half the first sampling frequency, that is, first sampling frequency/2. Furthermore, the changing unit 170 changes the signal flow used in the FFT operation by the fast Fourier transform unit 130 to a signal flow different from the signal flow illustrated in FIG. 3. More specifically, for example, in a case where the first algorithm is the algorithm of the FFT operation performed according to the signal flow illustrated in FIG. 3, the changing unit 170 substitutes results G[j] of even-numbered butterfly operations at a stage immediately before the final stage, that is, at a ($\log_2(N)-1$)th stage, into a linear regression model with an intercept aj and an inclination bj estimated by the statistical processing unit 150 thereby performing a regression calculation on results H[j] of odd-numbered butterfly operations at a ($\log_2(N)-1$)th stage, and then the changing unit 170 changes the algorithm to the second algorithm to perform butterfly operations at the final stage.

On the other hand, in a case where the correlation coefficient Sj is less than 0.7, it is determined that there is a high probability that the accuracy of the result of the calculation for the even-numbered data H using the linear regression model is lower than a particular level. In this case, the changing unit 170 maintains the first sampling frequency as the sampling frequency at which the sensor 11 and the ADC 12 operate, and maintains the first algorithm as the algorithm used in the FFT operation by the fast Fourier transform unit 130.

Figure 4:
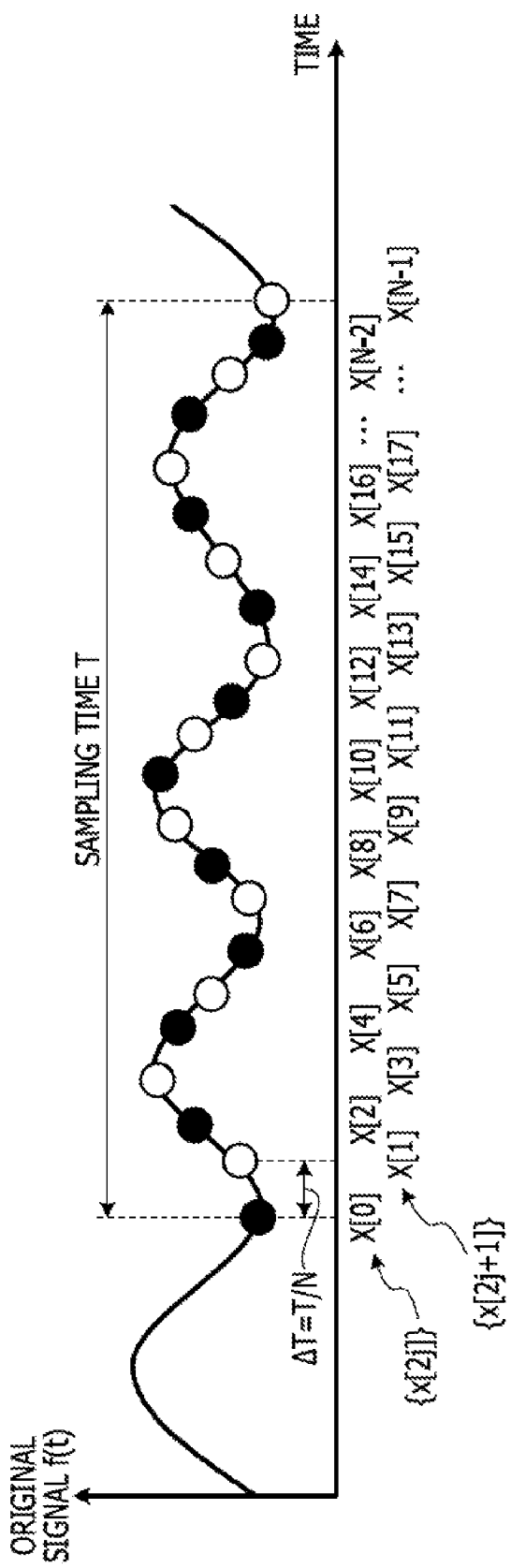
FIG. 4 is a diagram illustrating an example of even-numbered data and odd-numbered data.

<Correlation between even-numbered data and odd-numbered data> FIG. 4 is a diagram illustrating an example of even-numbered data and odd-numbered data. In FIG. 4, a vertical axis of a graph represents an amplitude value of a digital signal, and a horizontal axis of the graph represents time. In the example illustrated in FIG. 4, the length of time of input data subjected to the FFT operation performed by the fast Fourier transform unit 130 is equal to a sampling time T. The input data x(n) is divided into two groups one of which includes even-numbered data x(0), x(2), x(4), . . . x(N−2) represented by solid circles in FIG. 4 and generically denoted as x[2j], and the other one of which includes odd-numbered data x(1), x(3), x(5), . . . x(N−1) represented by open circles in FIG. 4 and generically denoted as x[2j+1].

Figure 5:
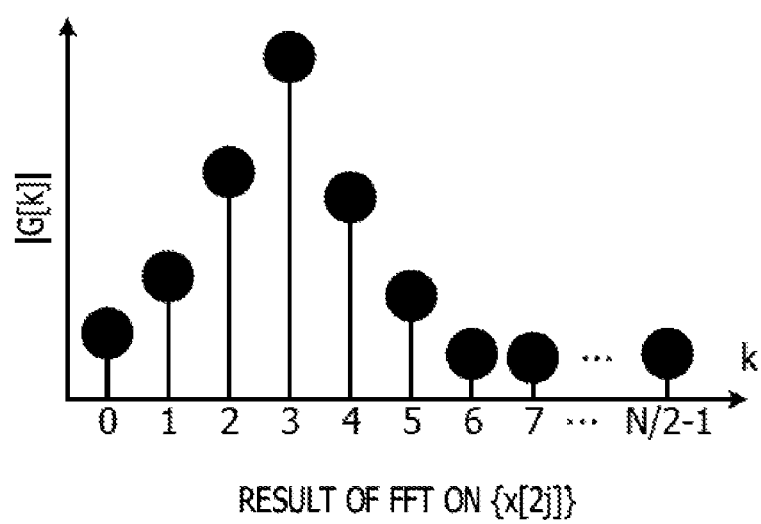
FIG. 5 is a diagram illustrating an example of a result of an N/2-point FFT operation.
Figure 6:
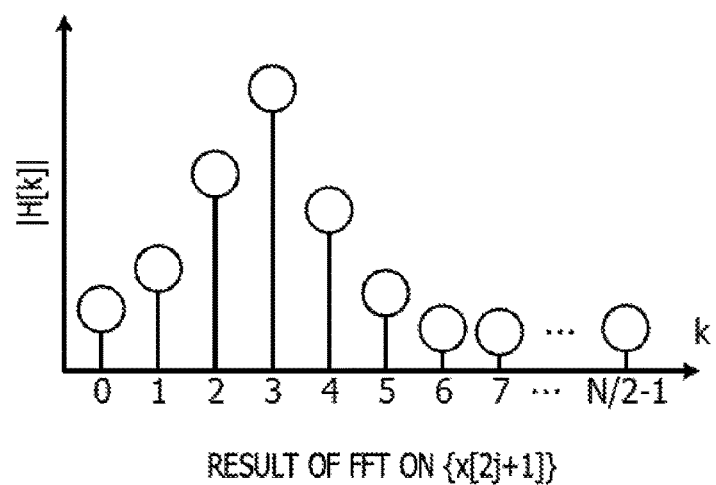
FIG. 6 is a diagram illustrating an example of a result of an N/2-point FFT operation.

FIG. 5 and FIG. 6 each illustrate an example of an N/2-point FFT operation. In the example illustrated in FIG. 5, the absolute value of each result G[k] is illustrated for a case where FFT is performed on x[2j] illustrated in FIG. 4. In the example illustrated in FIG. 6, the absolute value of each result H[k] is illustrated for a case where FFT is performed on x[2j+1] illustrated in FIG. 4. Note that the waveform of the absolute value of G[k] illustrated in FIG. 5 and the waveform of the absolute value of H[k] illustrated in FIG. 6 become more similar to each other as the sampling period ΔT (=T/N) decreases.

Figure 7:
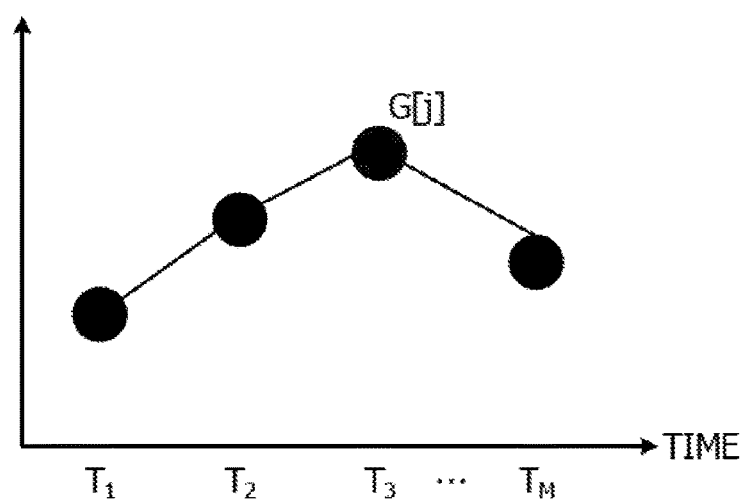
FIG. 7 is a diagram illustrating an example of input data over M generations.
Figure 8:
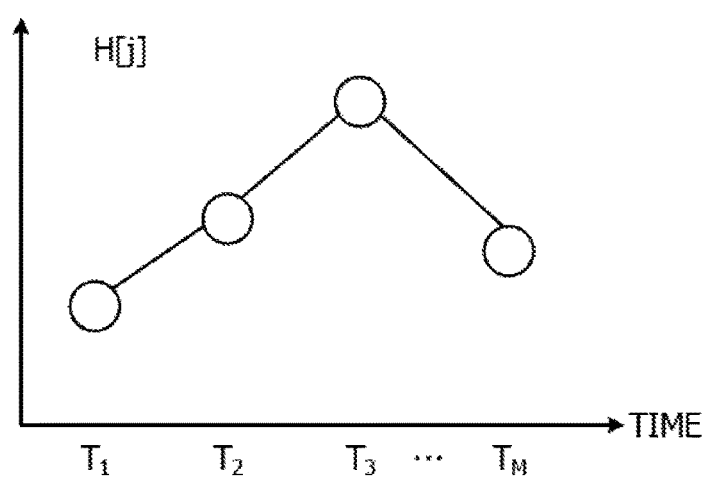
FIG. 8 is a diagram illustrating an example of input data over M generations.
Figure 9:
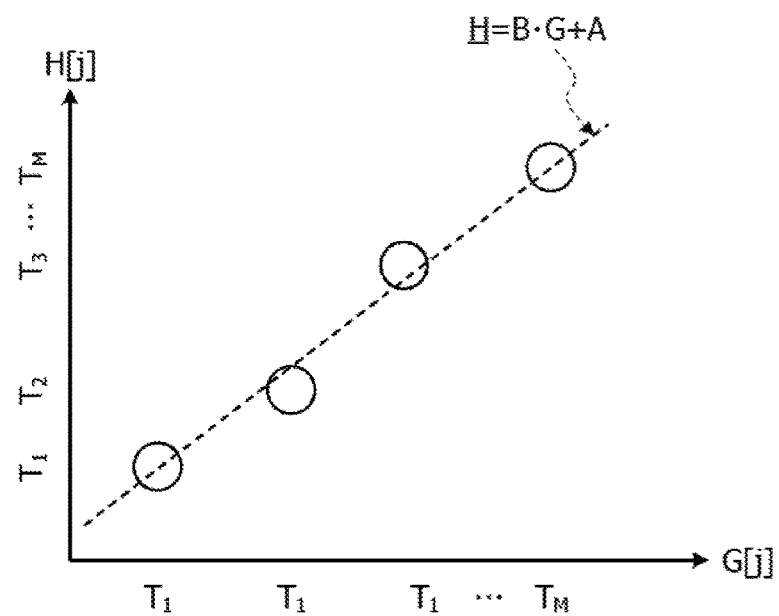
FIG. 9 is a diagram illustrating an example of a result of a regression analysis.

<Example of result of regression process> FIG. 7 and FIG. 8 each illustrate an example of input data over M generations. FIG. 9 illustrates an example of a result of a regression analysis. FIG. 7 illustrates results G[j] of even-numbered butterfly operations at a stage immediately before the final stage, that is, at a $(\log_2(N)-1)$th stage, over M generations (T=T1, . . . TM). FIG. 8 illustrates results H[j] of odd-numbered butterfly operations at the stage immediately before the final stage, that is, at the $(\log_2(N)-1)$th stage, over M generations (T=T1, . . . TM). In a case where the regression analysis is performed using G[j] illustrated in FIG. 7 and H[j] illustrated in FIG. 8, the result is such as that illustrated in FIG. 9. As illustrated in FIG. 9, a linear regression model "H=B·G+A" is obtained. In such a linear regression model, when the correlation coefficient S[j] between G[j] (T=Tk) and H[j] (T=Tk) is equal to or greater than a threshold value, for example, 0.7, if only new even-numbered data G is acquired, then, even if odd-numbered data H is not obtained, it is possible to calculate odd-numbered data H by substituting the acquired even-numbered data G into the linear regression model.

Figure 10:
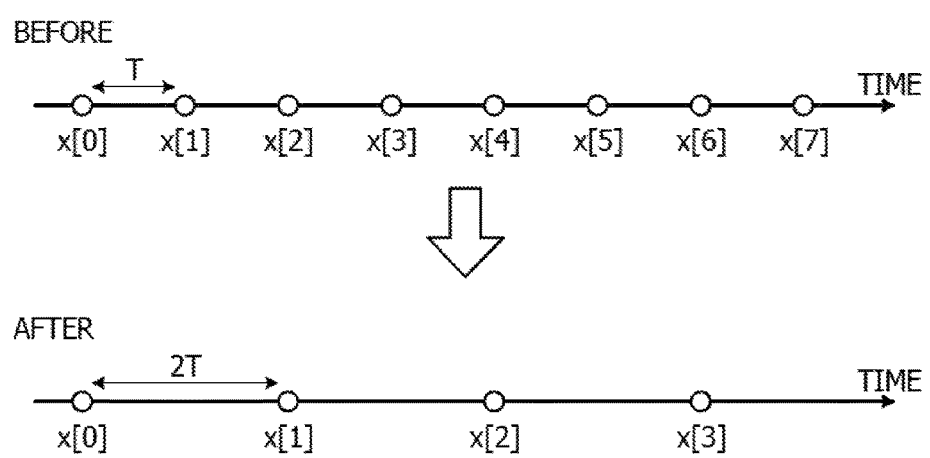
FIG. 10 is a diagram illustrating an example of a manner in which a sampling mode is changed.

<Changing sampling mode> FIG. 10 is a diagram illustrating an example of a manner of changing a sampling mode. In the sampling mode illustrated in an upper part of FIG. 10, the first sampling frequency is specified as the sampling frequency at which the sensor 11 and the ADC 12 operate. In the sampling mode illustrated in a lower part of FIG. 10, the second sampling frequency is specified as the sampling frequency at which the sensor 11 and the ADC 12 operate. That is, in a case where the correlation coefficient S[j] between G[j] (T=Tk) and H[j] (T=Tk) is equal to or greater than 0.7, the sampling frequency at which the sensor 11 and the ADC 12 operate is changed from the first sampling frequency to the second sampling frequency as illustrated in FIG. 10. When the sensor 11 and the ADC 12 operate at the second sampling frequency as described above, the sampling time is as large as the twice the sampling time T corresponding to the first sampling frequency illustrated in FIG. 4, that is, 2T.

Figure 11:
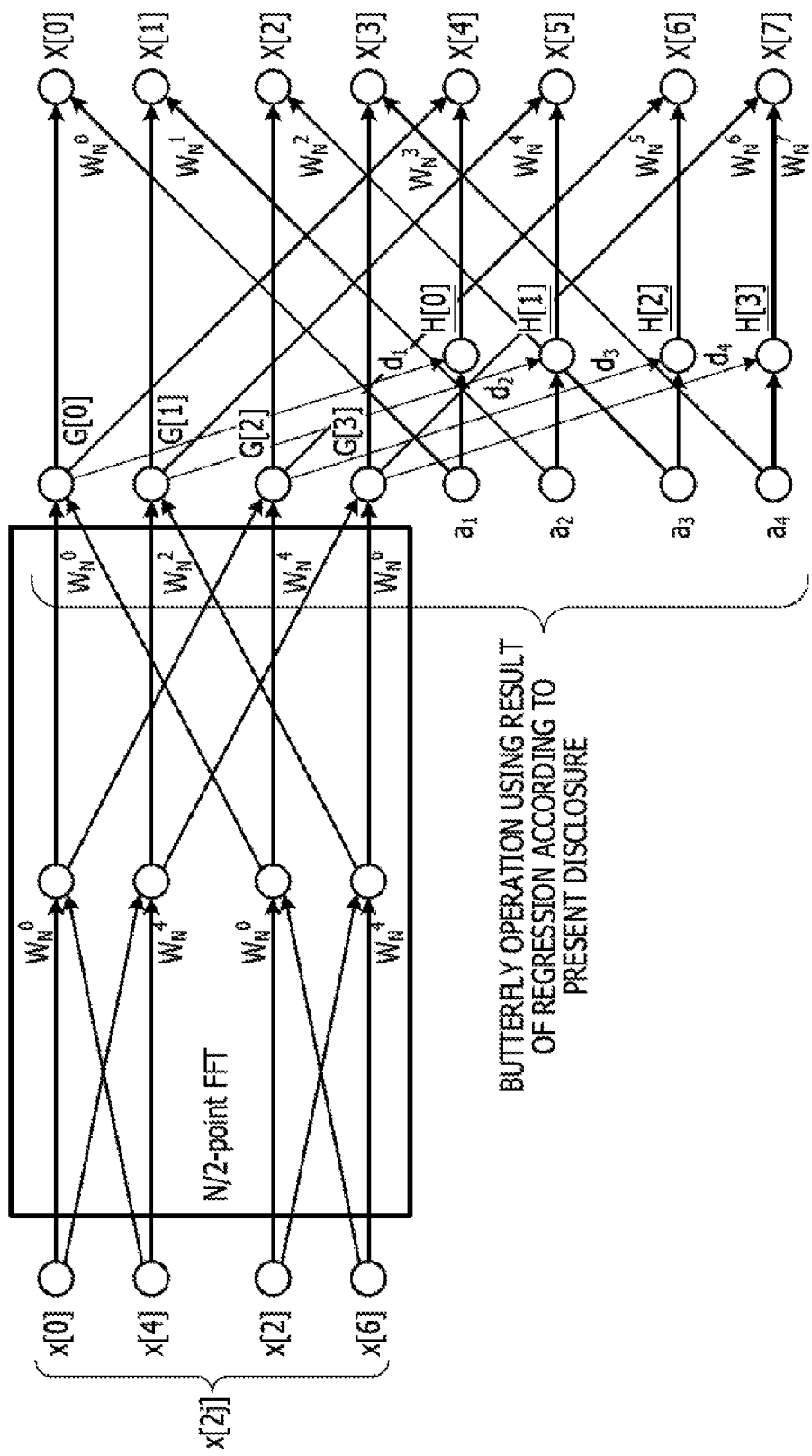
FIG. 11 is a diagram illustrating an example of a signal flow.

<Changing FFT operation algorithm> FIG. 11 illustrates an example of a signal flow. In FIG. 11, as in FIG. 3, the signal flow is illustrated by way of example for a case where N=8. In the signal flow illustrated in FIG. 11, unlike the signal flow illustrated in FIG. 3, input data sampled at the second sampling frequency, that is, input data sampled at a sampling period two times higher than the first sampling frequency, is input as x(0), x(2), x(4), and x(6). On the other hand, odd-numbered data at a stage immediately before the final state (that is, at the second stage in the present example) can be determined, by a regression calculation of a linear regression model, from even-numbered data at the second stage. From the even-numbered data and the odd-numbered data obtained in this way, the butterfly operation at the final stage, that is, at the third stage can be performed.

The amount of FFT operation O'(N) is given by the sum of the number of product operations and the number of addition operations, as described in formula (24). In formula (24), M'(N) denotes the number of product operations, and A'(N) denotes the number of addition operations. M'(N) is given by $N/2 \cdot \log_2(N)+N$ as described in formula (25) and formula (26), and A'(N) is also given by $N/2 \cdot \log_2(N)+N$ as described in formula (27) and formula (28). Therefore, the amount of FFT operation O'(N) is given by $N \cdot \log_2(N)+2 \cdot N$ as described in formula (29).

$$O'(N) = M'(N) + A'(N) \quad (24)$$
$$= N \cdot \log_2(N) + 2 \cdot N \quad (29)$$

$$\begin{cases} M'(N) = N \cdot \log_2(N) - N/2\log_2(N/2) + N/2 & (25) \\ \quad = N/2 \cdot \log_2(N) + N & (26) \\ A'(N) = N \cdot \log_2(N) - N/2\log_2(N/2) + N/2 & (27) \\ \quad = N/2 \cdot \log_2(N) + N & (28) \end{cases}$$

Thus, in the frequency analysis, when the number of pieces of data N is sufficiently large, the amount of FFT operation O'(N) is about one-half the amount of FFT operation O(N).

<Processing flow> Next, a flow of processing performed by the sensor module 10 according to the present embodiment is described below. More specifically, (1) flow of controlling hardware by the MCU 100 is first described, and then (2) sequence of controlling the sensor module 10 is described, and (3) frequency analysis process is described. Subsequently, (4) first FFT process performed according to the signal flow illustrated in FIG. 3 is described, and then (5) second FFT process performed according to the signal flow illustrated in FIG. 10 is described.

Figure 12:
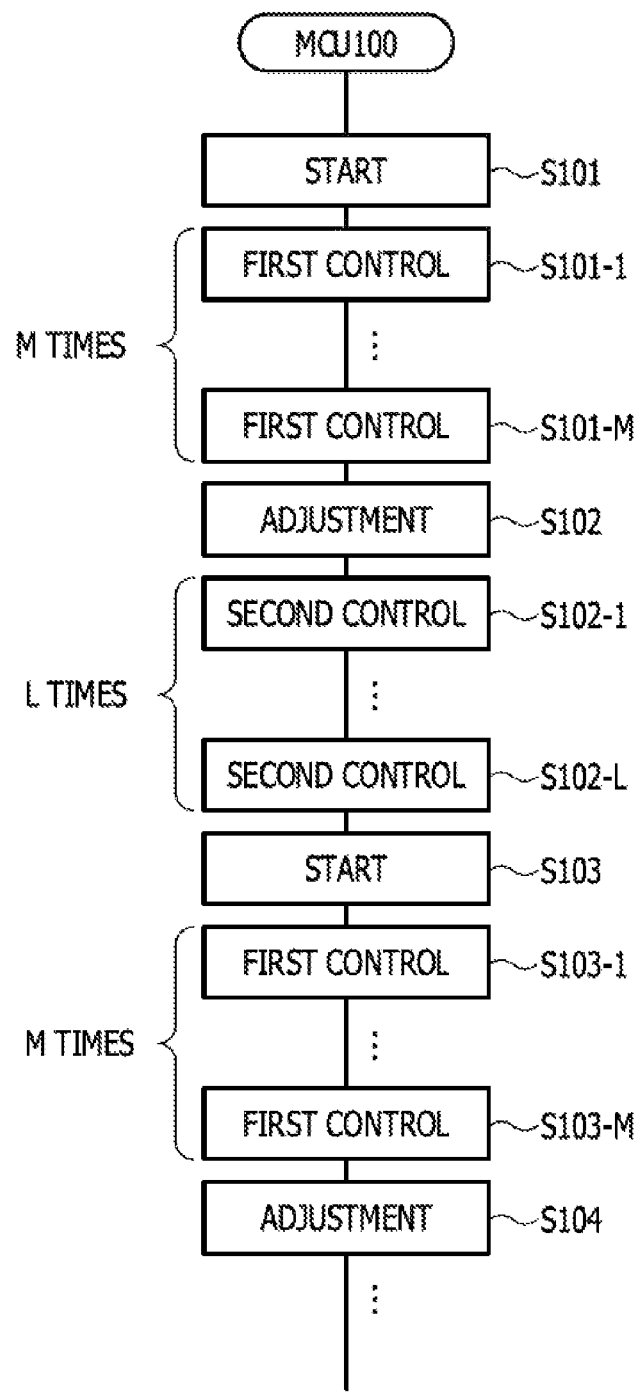
FIG. 12 is a diagram illustrating an example of a flow of controlling hardware according to the first embodiment.

<1. Flow of controlling hardware> FIG. 12 is a diagram illustrating an example of a flow of controlling hardware according to the first embodiment. As illustrated in FIG. 12, when the power of the sensor module 10 is turned on, the MCU 100 starts controlling hardware (step S101). For example, the MCU 100 performs repeatedly (M times) a first control in which the sampling frequency at which the sensor 11 and the ADC 12 operate is set to the first sampling frequency, and the algorithm used in the FFT operation by the fast Fourier transform unit 130 is set to the first algorithm (steps S101-1 to S101-M).

Thereafter, the MCU 100 performs an adjustment such that, depending on whether the correlation coefficient Sj obtained as a result of the frequency analysis process described above is in a range equal to or greater than 0.7, the first control is maintained or the sampling frequency at which the sensor 11 and the ADC 12 operate is set to the second sampling frequency and the algorithm used in the FFT operation by the fast Fourier transform unit 130 is set to the second algorithm (step S102).

Here, it is assumed by way of example that the correlation coefficient Sj is equal to or greater than 0.7. In this case, the MCU 100 performs second control repeatedly a predetermined times (L times) such that in each iteration of the second control, the sampling frequency at which the sensor 11 and the ADC 12 operate is set to the second sampling frequency, and the algorithm used in the FFT operation by the fast Fourier transform unit 130 is set to the first algorithm (steps S102-1 to S102-L). Note that when the correlation coefficient Sj is less than 0.7, the first control is maintained and steps similar to steps S101-1 to S101-M are performed.

Thereafter, the MCU 100 performs the frequency analysis process described above. If a condition to end the second control is satisfied, the first control is started (step S103) and the MCU 100 performs the first control described above repeatedly M times (steps S103-1 to S103-M).

Thereafter, the MCU 100 performs an adjustment as to whether the first control is maintained or the control is changed from the first control to the second control (step S104). In this step, if the correlation coefficient Sj is equal to or greater than 0.7, the first control is changed to the second control, but when the correlation coefficient Sj is less than 0.7, the first control is maintained.

The MCU 100 controls the hardware in the sensor module 10 as described above. In the example described above, the end condition to end the second control is defined by way of example by the upper limit of the number of iterations of the process. Alternatively, the end condition to end the second control may be defined by an elapsed time or the like.

Figure 13:
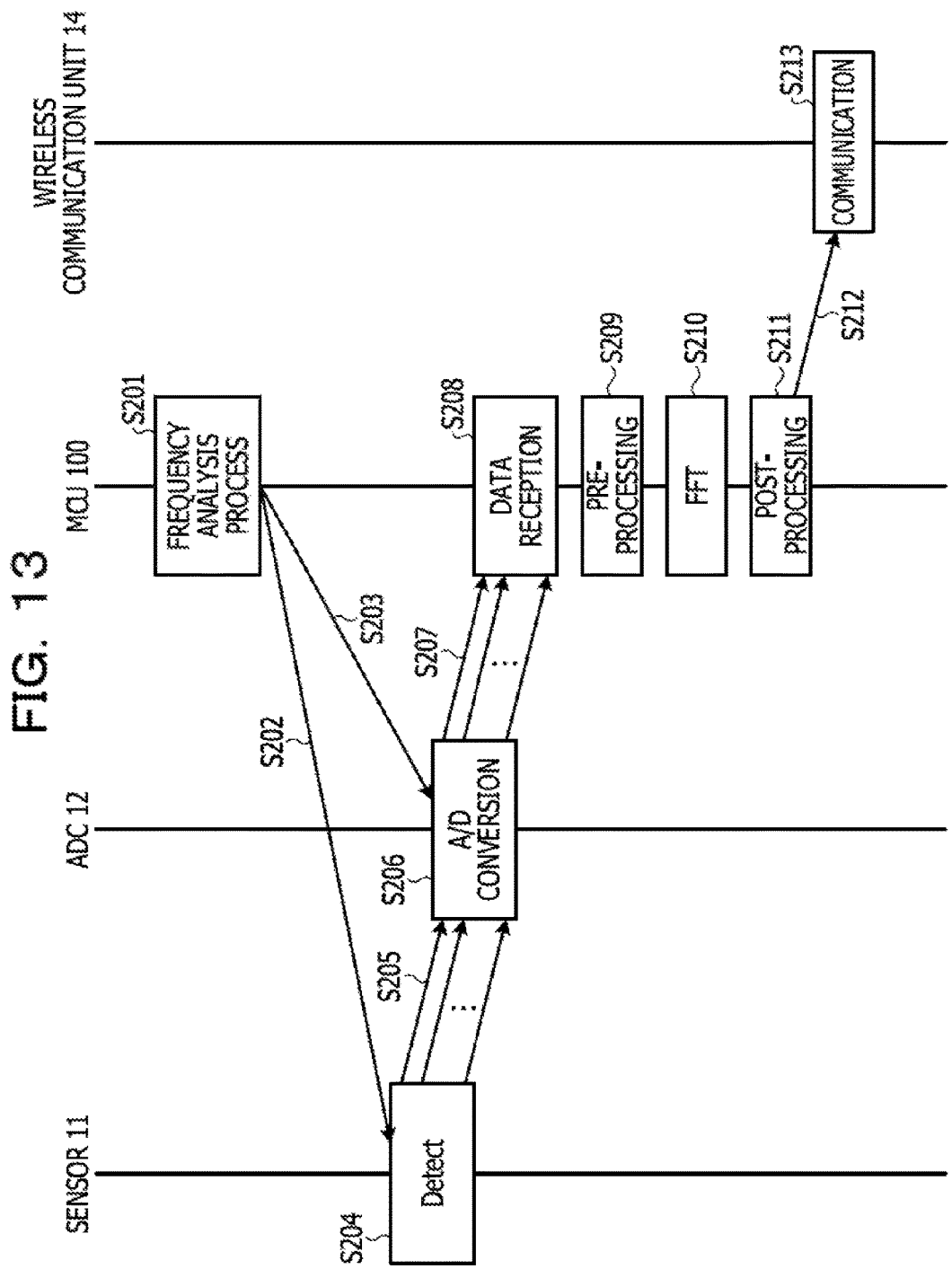
FIG. 13 is a diagram illustrating an example of a sequence of controlling a sensor module according to the first embodiment.

<2. Sequence of controlling sensor module 10> FIG. 13 is a diagram illustrating an example of a sequence of controlling the sensor module 10 according to the first embodiment. The control sequence illustrated in FIG. 13 is performed in a process corresponding to step S102 or step S104 illustrated in FIG. 12.

As illustrated in FIG. 13, the MCU 100 performs the frequency analysis process described above, and determines which one of the first control and the second control is to be performed (step S201). According to the result of the determination made in step S201, the MCU 100 specifies the sampling mode to be employed by the sensor 11 and the ADC 12, that is, instructs the sensor 11 and the ADC 12 to employ the first sampling frequency or the second sampling frequency (step S202 and step S203).

Subsequently, the sensor 11 senses data with a length corresponding to a sampling time T at a sampling frequency specified in step S202 (step S204), and transmits resultant data to the ADC 12 (step S205). The ADC 12 performs an analog-to-digital conversion on the data received in step S205 at the sampling frequency specified in step S203 (step S206), and transmits resultant N or N/2 pieces of data to the MCU 100 (step S207).

The MCU 100 receives the N or N/2 pieces of data transmitted in step S207 (step S208). The pre-processing unit 130A performs a pre-processing on the N or N/2 pieces of data received in step S208 (step S209), and the fast Fourier transform unit 130 performs a fast Fourier transform on the N or N/2 pieces of data subjected to the pre-processing in step S209 (step S210).

Thereafter, the post-processing unit 130B performs a post-processing on the result of the fast Fourier transform obtained in step S210 (step S211), and outputs the result of the post-processing to the wireless communication unit 14 (step S212). The wireless communication unit 14 transmits the result of the post-processing received from the MCU 100 in step S212 to a particular output destination (step S213). Thereafter, the process is ended.

Figure 14:
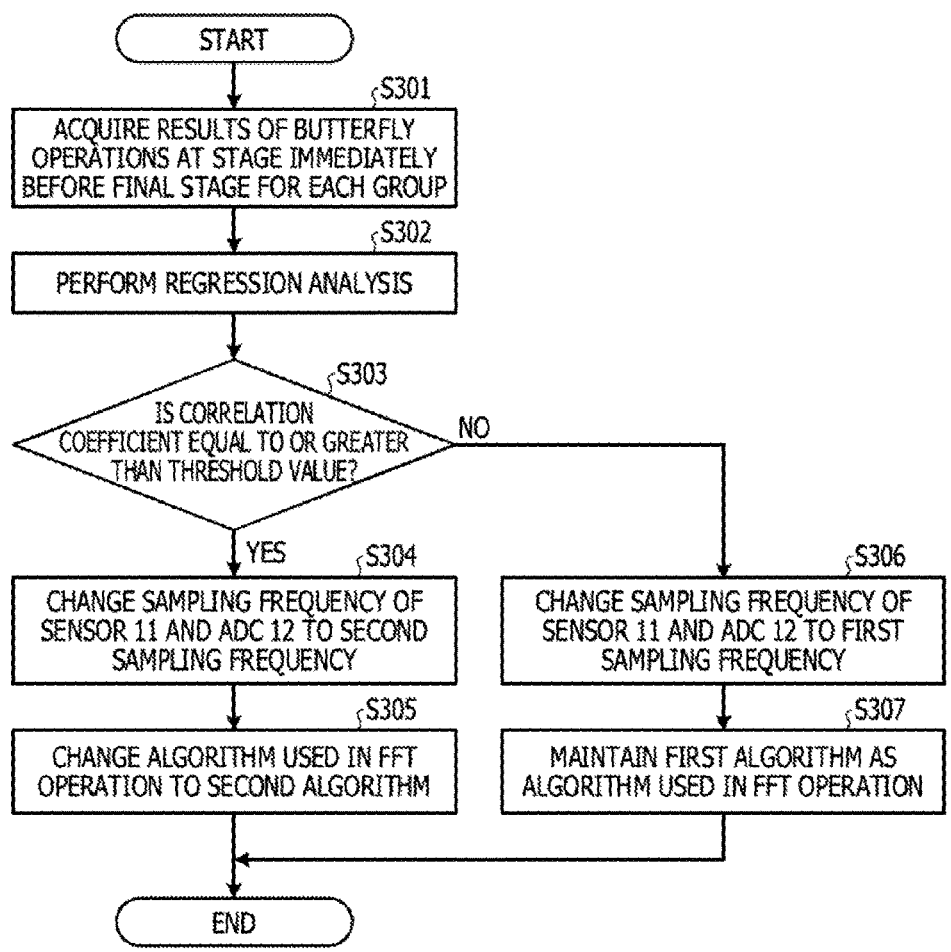
FIG. 14 is a flow chart illustrating a procedure of a frequency analysis process according to the first embodiment.

<3. Frequency analysis process> FIG. 14 is a flow chart illustrating a procedure of a frequency analysis process according to the first embodiment. The process illustrated in FIG. 14 corresponds to step S201 in FIG. 13. As illustrated in FIG. 14, the statistical processing unit 150 reads, from the memory 110, the result G[k] of the even-numbered N/2-point butterfly operation at the stage immediately before the final stage, that is, at the $(\log_2(N)-1)$th stage and the result H[k] of the odd-numbered N/2-point butterfly operation at the stage immediately before the final stage over M generations (T=T1, . . . TM) (step S301).

Thereafter, the statistical processing unit 150 performs a regression analysis on the result G[k] of the butterfly operation at the stage immediately before the final stage and the result H[k] of the butterfly operation at the stage immediately before the final stage read out in step S301 over the M generations (T=T1, . . . TM) (step S302). As a result, a regression analysis result {aj, bj, Sj} is obtained.

The changing unit 170 then determines whether the correlation coefficient Sj obtained as a result of the regression analysis in step S302 is equal to or grater than a predetermined threshold value (step S303).

In a case where the correlation coefficient Sj is equal to or greater than the threshold value (Yes in step S303), it is determined that there is a high probability that the accuracy of the calculation result of H[k] using the linear regression model is equal to or higher than a particular level. In this case, the changing unit 170 changes the sampling frequency at which the sensor 11 and the ADC 12 operate to the second sampling frequency (step S304).

Furthermore, the changing unit 170 changes the algorithm used in the FFT operation by the fast Fourier transform unit 130 to the second algorithm (step S305). Thereafter, the process is ended.

On the other hand, in a case where the correlation coefficient Sj is less than the threshold value (No in step S303), it is determined that there is a high probability that the accuracy of the result of the calculation for the even-numbered data H using the linear regression model is lower than a particular level. In this case, the changing unit 170 maintains the first sampling frequency as the sampling frequency at which the sensor 11 and the ADC 12 operate (step S306), and furthermore the changing unit 170 maintains the first algorithm as the algorithm used in the FFT operation by the fast Fourier transform unit 130 (step S307). Thereafter, the process is ended.

Figure 15:
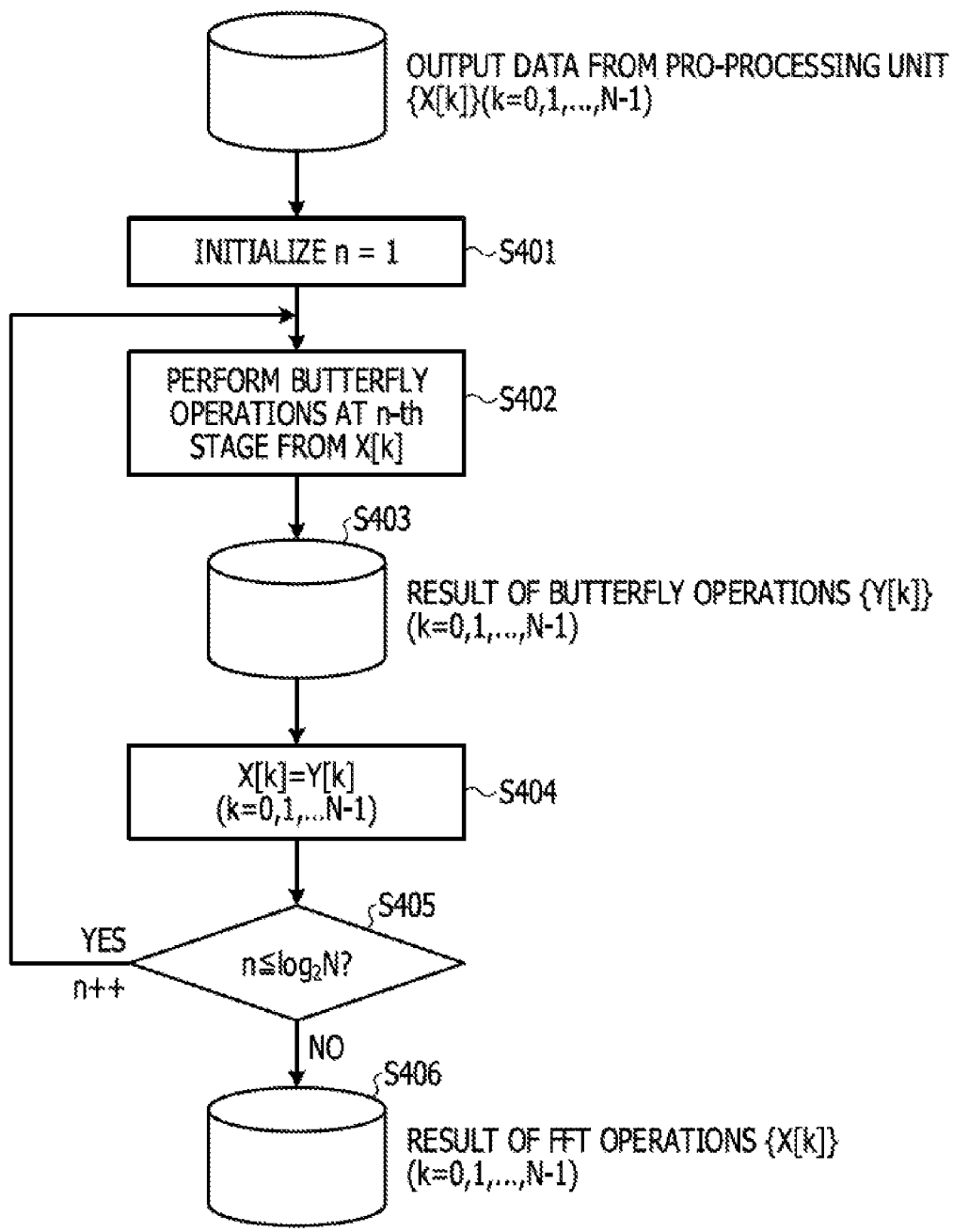
FIG. 15 is a flow chart illustrating a procedure of a first FFT process according to the first embodiment.

<4. First FFT process> FIG. 15 is a flow chart illustrating a procedure of a first FFT process according to the first embodiment. This process is performed, by way of example, in a case where in step S307 illustrated in FIG. 14, the first algorithm is maintained as the algorithm used in the FFT operation by the fast Fourier transform unit 130, and this process is started when the output data {X[k]} (k=0, 1, . . . , N−1) of the pre-processing unit 130A is read out from the memory 110.

As illustrated in FIG. 15, the fast Fourier transform unit 130 initializes the index n indicating the stage number in the signal flow to "1" (step S401). Subsequently, the fast Fourier transform unit 130 performs the butterfly operation at the n-th stage from X[k] (step S402). The fast Fourier transform unit 130 then stores the result {Y[k]} of the butterfly operation performed in step S402 in the memory 110 (step S403). Subsequently, the fast Fourier transform unit 130 substitutes the butterfly operation result {Y[k]} obtained in step S402 into X[k] (step S404).

In a case where the index n indicating the stage number in the signal flow is equal to or smaller than $\log_2(N)$, that is, in a case where the final stage has not been reached yet (Yes in step S405), the index n indicating the stage number in the signal flow is incremented, and the process from step S402 to step S404 is performed repeatedly.

Thereafter, in a case where the index n indicating the stage number in the signal flow becomes larger than $\log_2(N)$, that is, in a case where the final stage is reached (No in step S405), the fast Fourier transform unit 130 determines X[k] stored in the memory 110 as the final result of the FFT operation (step S406), and the process is ended.

Figure 16:
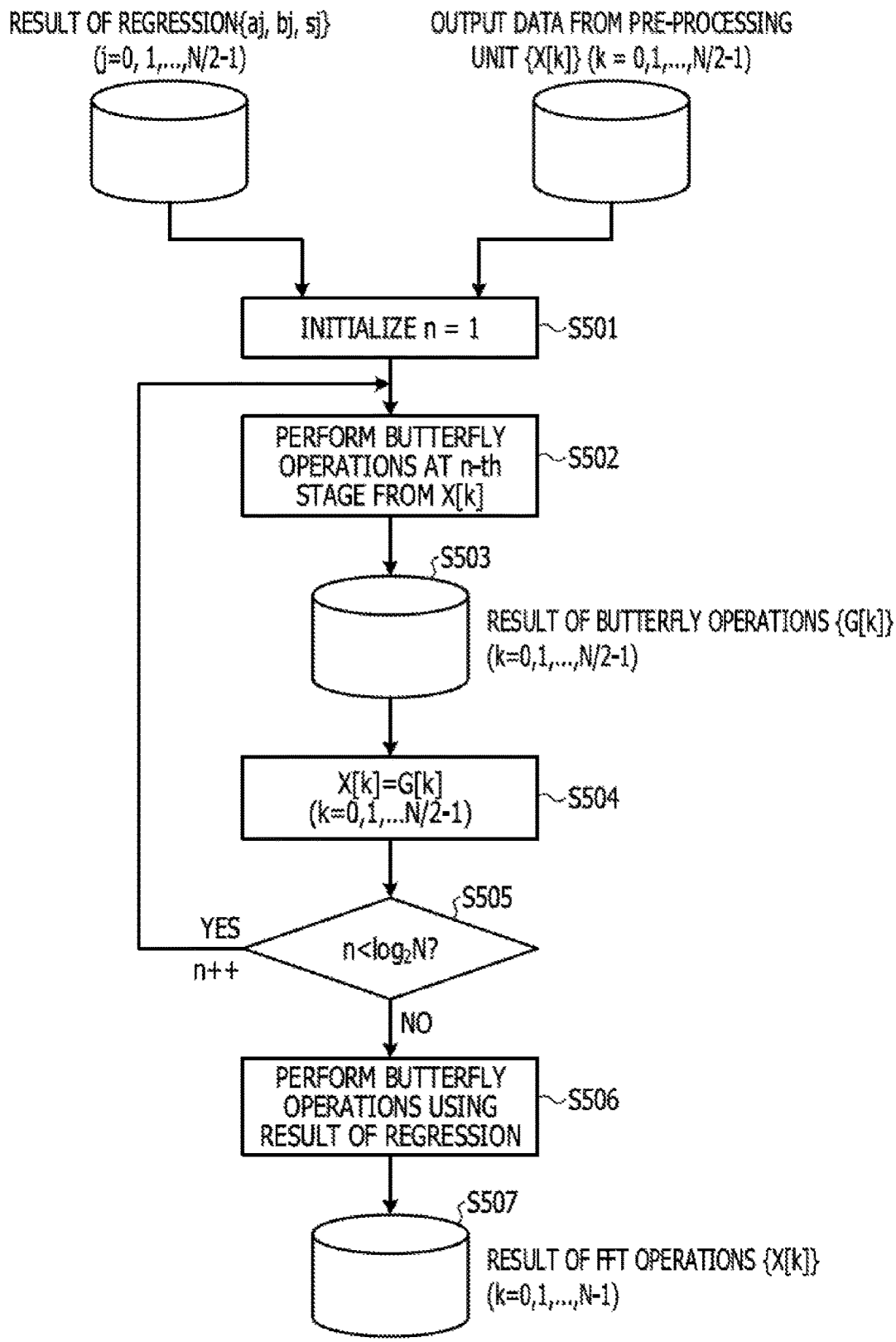
FIG. 16 is a flow chart illustrating a procedure of a second FFT process according to the first embodiment.

<5. Second FFT process> FIG. 16 is a flow chart illustrating a procedure of a second FFT process according to the first embodiment. This process is performed, by way of example, in a case where in step S305 illustrated in FIG. 14, the algorithm used in the FFT operation by the fast Fourier transform unit 130 is changed to the second algorithm, and this process is started when the output data {X[k]} (k=0, 1, . . . , N/2−1) of the pre-processing unit 130A and the regression analysis result {aj, bj, Sj} are read out from the memory 110.

As illustrated in FIG. 16, the fast Fourier transform unit 130 initializes the index n indicating the stage number in the signal flow to "1" (step S501). Subsequently, the fast Fourier transform unit 130 performs the butterfly operation at the n-th stage from X[k] (step S502). The fast Fourier transform unit 130 then stores the results {G[k]} (k=0, 1, . . . , N/2−1) of the even-numbered butterfly operations performed in step S502 in the memory 110 (step S503). Subsequently, the fast Fourier transform unit 130 substitutes the butterfly operation results {G[k]} obtained in step S502 into X[k] (step S504).

In a case where the index n indicating the stage number in the signal flow is smaller than $\log_2(N)$, that is, in a case where the stage immediately before the final stage has not been reached yet (Yes in step S505), the index n indicating the stage number in the signal flow is incremented, and the process from step S502 to step S504 is performed repeatedly.

Thereafter, if the index n indicating the stage number in the signal flow becomes equal to or greater than $\log_2(N)$, that is, in a case where the stage immediately before the final stage is reached (No in step S505), the fast Fourier transform unit 130 then performs a process as described below. That is, the fast Fourier transform unit 130 substitutes the result G[j] of the even-numbered butterfly operation at the stage immediately before the final stage, that is, at the $(\log_2(N)-1)$th stage, into the linear regression model thereby determining the results H[j] of the odd-numbered butterfly operations at the $(\log_2(N)-1)$th stage, and then the fast Fourier transform unit 130 performs the butterfly operations at the final stage, that is, at the $(\log_2(N))$th stage from the results G[j] and H[j] of the even-numbered and odd-numbered butterfly operations at the stage immediately before the final stage (step S506). Thereafter, the fast Fourier transform unit 130 stores the results X[k] (k=0, 1, . . . , N−1) of the butterfly operations at the $(\log_2(N))$th stage performed in step S506 as the results of the FFT operations in the memory 110 (step S507), and the process is ended.

In the present embodiment, as described above, the MCU 100 performs the frequency analysis process including the fast Fourier transform on data of two groups into which sensor data obtained at the first sampling frequency is divided. If the butterfly operation results thereof are similar between the two groups, the sampling frequency at which the sensor 11 and the like operate is changed to the second sampling frequency lower than the first sampling frequency. Therefore, in an aspect, the MCU 100 according to the present embodiment is capable of reducing the frequency of occurrences of the operation of the ADC 12 to convert data in the sensor 11 and data input from the sensor 11 from analog form to digital form thereby achieving a reduction in consumption power of the sensor module 10.

Furthermore, in the MCU 100 according to the present embodiment, using input data of one of two groups, data of the other one of the two groups is determined by performing the regression calculation according to the regression model estimated from the result of the butterfly operation at the stage immediately before the final stage, and then the butterfly operation for the final stage is performed. In the MCU 100 according to the present embodiment, part of the butterfly operation performed in the fast Fourier transform is replaced by the regression calculation as described above, it is possible to reduce the amount of butterfly operation. Thus, the MCU 100 according to the present embodiment is capable of more effectively reducing the consumption power of the sensor module 10.

Second Embodiment

The apparatus according to the present disclosure has been described above with reference to the embodiment. However, the present disclosure is not limited to the embodiment described above, and many other embodiments may be possible. Some examples of other embodiments according to the present disclosure are described below.

<Application to general-purpose computer system> In the first embodiment described above, the frequency analysis process is implemented, by way of example but not limitation, in the built-in system. Also in a general-purpose computer system such as a personal computer, a server apparatus, or the like, the consumption power of the apparatus increases as the amount of the fast Fourier transform operation increases. Thus, by employing the second FFT process, it is possible to reduce the amount of the fast Fourier transform operation thereby reducing the consumption power.

<Distribution and integration> Note that the physical configurations of constituent elements of each apparatus are not limited to those described in the figures. That is, the configurations in terms of distribution or integration of apparatuses are not limited to those described in the figures, but all or part of constituent elements may be functionally or physically distributed or integrated depending the state of the load or usage. For example, part of the functional units of the sensor module 10 or part of the processing units of the MCU 100 may be disposed as an external apparatus outside the sensor module 10 or the MCU 100 and the external apparatus may be connected via a network.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention. For example, the steps recited in any of the method or process descriptions may by executed in any order and are not limited to the order presented.

What is claimed is:

1. An apparatus for controlling a frequency analysis processing, the apparatus comprising:
a memory; and
a processor coupled to the memory and configured to execute a process that includes acquiring time sequential data sensed at a first sampling frequency by a sensor and dividing the time sequential data into a first group and a second group in accordance with sequential order of the time sequential data, the first group including first data having first time sequential order of the time sequential data, the second group including second data having second time sequential order of the time sequential data, execute a fast Fourier transform process that includes performing a fast Fourier transform operation on the first group and the second group and acquiring similarity degree between a first result of a butterfly operation for the first group and a second result of the butterfly operation for the second group, and execute a change process that includes changing, in a case where the similarity degree is at least equal to a given threshold, a sampling frequency at which the sensor operates to a second sampling frequency lower than the first sampling frequency.

2. The apparatus according to claim 1, wherein the processor is further configured to execute a statistical process that includes estimating a regression model by which to determine the second result of the butterfly operation for the second group of the two groups from the first result of the butterfly operation executed in the fast Fourier transform operation for the first group of the two groups, and wherein the change process includes changing an algorithm used in the fast Fourier transform operation to an algorithm in which part of the butterfly operation associated with the second group is replaced by a regression result of a regression calculation determined from the regression model.

3. The apparatus according to claim 2, wherein the statistical process includes estimating a regression model by which it is allowed to determine the second result of the butterfly operation at a stage immediately before a final stage for the second group from the first result of the butterfly operation at the stage immediately before the final stage for the first group, and wherein the change process includes changing to an algorithm in which the butterfly operation at the stage immediately before the final stage associated with the second group is replaced by the regression result of the regression calculation determined from the regression model.

4. The apparatus according to claim 3, wherein the statistical process includes estimating the regression model by performing a regression analysis based on a least square method.

5. The apparatus according to claim 4, wherein the change process includes changing the sampling frequency at which the sensor operates to the first sampling frequency, in a case where after the sampling frequency at which the sensor operates is changed to the second sampling frequency, a predetermined period of time has passed, or the fast Fourier transform operation is performed a predetermined number of times.

6. The apparatus according to claim 1, wherein the first group includes odd-numbered data of the time sequential data, and the second group includes even-numbered data of the time sequential data.

7. A method for controlling a frequency analysis process, the method comprising:

executing a process that includes acquiring time sequential data sensed at a first sampling frequency by a sensor and dividing the time sequential data into a first group and a second group in accordance with sequential order of the time sequential data, the first group including first data having first time sequential order of the time sequential data, the second group including second data having second time sequential order of the time sequential data executing, by a processor, a fast Fourier transform process that includes performing a fast Fourier transform operation on the first group and the second group and acquiring similarity degree between a first result of a butterfly operation for the first group and a second result of the butterfly operation for the second group; and executing, by the processor, a change process that includes changing, in a case where the similarity degree is at least equal to a given threshold, a sampling frequency at which the sensor operates to a second sampling frequency lower than the first sampling frequency.

8. The method according to claim 7, further comprising:

executing, by the processor, a statistical process that includes estimating a regression model by which to determine the second result of the butterfly operation for the second group from the first result of the butterfly operation executed in the fast Fourier transform for the first group of the two groups, and wherein the change process executed by the processor includes changing an algorithm used in the fast Fourier transform operation to an algorithm in which part of the butterfly operation associated with the second group is replaced by a regression result of a regression calculation determined from the regression model.

9. The method according to claim 8, wherein the statistical process executed by the processor includes estimating a regression model by which it is allowed to determine the second result of the butterfly operation at a stage immediately before a final stage for the second group from the first result of the butterfly operation at the stage immediately before the final stage for the first group, and wherein the change process executed by the processor includes changing to an algorithm in which the butterfly operation at the stage immediately before the final stage associated with the second group is replaced by the result of the regression calculation determined from the regression model.

10. The method according to claim 9, wherein the statistical process executed by the processor includes estimating the regression model by performing a regression analysis based on a least square method.

11. The method according to claim 10, wherein the change process executed by the processor includes changing the sampling frequency at which the sensor operates to the first sampling frequency, in a case where after the sampling frequency at which the sensor operates is changed to the second sampling frequency, a predetermined period of time has passed, or the fast Fourier transform is performed a predetermined number of times.

12. A sensor module comprising:

a sensor configured to sense sensor data at a first sampling frequency; and a frequency analysis apparatus having a processor configured to execute a process that includes acquiring time sequential data sensed at a first sampling frequency by a sensor and dividing the time sequential data into a first group and a second group in accordance with sequential order of the time sequential data, the first group including first data having first time sequential order of the time sequential data, the second group including second data having second time sequential order of the time sequential data, execute a fast Fourier transform process that includes performing a fast Fourier transform operation on the first group and the second group and acquiring similarity degree between a first result of a butterfly operation for the first group and a second result of the butterfly operation for the second group, and execute a change process that includes changing, in a case where the similarity degree is at least equal to a given threshold, a sampling frequency at which the sensor operates to a second sampling frequency lower than the first sampling frequency.

13. The sensor module according to claim 12, wherein the processor of the frequency analysis apparatus is further configured to execute a statistical process that includes estimating a regression model by which to determine a second result of the butterfly operation for the second group from a first result of the butterfly operation executed in the fast Fourier transform for the first group of the two groups, and wherein the change process executed by the processor of the frequency analysis apparatus includes changing an algorithm used in the fast Fourier transform operation to an algorithm in which part of the butterfly operation associated with the second group is replaced by a regression result of a regression calculation determined from the regression model.

14. The sensor module according to claim 13, wherein the statistical process executed by the processor of the frequency analysis apparatus includes estimating the regression model by performing a regression analysis based on a least square method.

15. The sensor module according to claim 14, wherein the change process executed by the processor of the frequency analysis apparatus includes changing the sampling frequency at which the sensor operates to the first sampling frequency, in a case where after the sampling frequency at which the sensor operates is changed to the second sampling frequency, a predetermined period of time has passed, or the fast Fourier transform is performed a predetermined number of times.

* * * * *